United States Patent
Han et al.

(10) Patent No.: US 10,676,768 B2
(45) Date of Patent: Jun. 9, 2020

(54) MUTANT MICROORGANISM FOR PRODUCING L-CYSTEINE AND METHOD FOR PRODUCING L-CYSTEINE USING SAME

(71) Applicant: KOREA UNIVERSITY RESEARCH AND BUSINESS FOUNDATION, Seoul (KR)

(72) Inventors: Sung Ok Han, Seoul (KR); Young-Chul Joo, Seoul (KR); Jeong-Eun Hyeon, Seoul (KR); Seung-Kyou You, Jeonju-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/069,307

(22) PCT Filed: Dec. 7, 2016

(86) PCT No.: PCT/KR2016/014282
§ 371 (c)(1),
(2) Date: Jul. 11, 2018

(87) PCT Pub. No.: WO2017/122931
PCT Pub. Date: Jul. 20, 2017

(65) Prior Publication Data
US 2019/0284591 A1    Sep. 19, 2019

(30) Foreign Application Priority Data
Jan. 15, 2016    (KR) .......................... 10-2016-0005378

(51) Int. Cl.
*C12P 13/12*       (2006.01)
*C12N 9/10*        (2006.01)
(Continued)

(52) U.S. Cl.
CPC .............. *C12P 13/12* (2013.01); *C07K 14/34* (2013.01); *C12N 9/0051* (2013.01); *C12N 9/10* (2013.01);
(Continued)

(58) Field of Classification Search
None
See application file for complete search history.

(56) References Cited

U.S. PATENT DOCUMENTS

2002/0086373 A1    7/2002  Farwick et al.

FOREIGN PATENT DOCUMENTS

EP         0 307 247 A2       3/1989
KR     10-2005-0018797 A      2/2005
(Continued)

OTHER PUBLICATIONS

Denk, Dagmar, et al. "L-Cysteine Biosynthesis in *Escherichia coli*: Nucleotide Sequence and Expression of the Serine Acetyltransferase (cysE) Gene from the Wild-type and a Cysteine-excreting Mutant", *Journal of General Microbiology*, 1987, vol. 133, pp. 515-525.
(Continued)

*Primary Examiner* — Yong D Pak
(74) *Attorney, Agent, or Firm* — NSIP Law

(57) ABSTRACT

The present invention relates to an L-cysteine-producing mutant microorganism having introduced therein genes encoding enzymes which are involved in the L-cysteine metabolic pathway, and more particularly to an L-cysteine-producing mutant microorganism having introduced therein cysE, cysK and cysR, which are genes encoding enzymes which are involved in the L-cysteine metabolic pathway, and to a method of producing L-cysteine using the mutant microorganism. According to the present invention, L-cysteine can be produced with high efficiency as a result of regulating metabolic fluxes associated with the L-cysteine
(Continued)

metabolic pathway of the mutant microorganism and regulating a system for supplying a sulfur source essential for synthesis of L-cysteine.

2 Claims, 13 Drawing Sheets

Specification includes a Sequence Listing.

(51) Int. Cl.
*C12N 1/20* (2006.01)
*C12N 15/00* (2006.01)
*C07H 21/04* (2006.01)
*C07K 1/00* (2006.01)
*C12N 9/02* (2006.01)
*C12N 15/77* (2006.01)
*C07K 14/34* (2006.01)
*C12N 15/52* (2006.01)

(52) U.S. Cl.
CPC ......... *C12N 9/1029* (2013.01); *C12N 9/1085* (2013.01); *C12N 15/52* (2013.01); *C12N 15/77* (2013.01); *C12Y 108/01006* (2013.01); *C12Y 203/0103* (2013.01); *C12Y 205/01047* (2013.01)

(56) References Cited

FOREIGN PATENT DOCUMENTS

WO      WO 91/08291 A2    6/1991
WO      WO 2005/083082 A1   9/2005

OTHER PUBLICATIONS

Nakamori, Shigeru, et al. "Overproduction of L-Cysteine and L-Cystine by *Escherichia coli* Strains with a Genetically Altered Serine Acetyltransferase", *Applied and Environmental Microbiology*, May 1998, vol. 64, No. 5, pp. 1607-1611.

Takagi, Hiroshi, et al. "Overproduction of L-cysteine and L-cystine by expression of genes for feedback inhibition-insensitive serine acetyltransferase from *Arabidopsis thaliana* in *Escherichia coli*", *FEMS Microbiology Letters* 179, 1999, pp. 453-459.

Takagi, Hiroshi, et al. "PCR random mutagenesis into *Escherichia coli* serine acetyltransferase: isolation of the mutant enzymes that cause overproduction of L-cysteine and L-cystine due to the desensitization to feedback inhibition", *FEBS Letters* 452, 1999, pp. 323-327.

Wirtz, M., et al. "Production of cysteine for bacterial and plant biotechnology: Application of cysteine feedback-insensitive isoforms of serine acetyltransferase", *Amino Acids*, 2003, vol. 24, pp. 195-203.

Nakatani, Takeshi, et al. "Enhancement of thioredoxin/glutaredoxinmediated L-cysteine synthesis from S-sulfocysteine increases L-cysteine production in *Escherichia coli*", *Microbial Cell Factories*, 2012, vol. 11, Issue 62, pp. 1-9.

GenBank: CP005959.1, Corynebacterium glutamicum MB001, complete genome, Appl. Environ. Microbiol., Jan. 2014, (3 pages in English).

Lee, Dong-Seok, et al. "Corynebacterium glutamicum sdhA encoding succinat dehydrogenase subunit A plays a role in cysR-mediated sulfur metabolism", *Appl Microbiol Biotechnol*, 2014, vol. 98, pp. 6751-6759.

International Search Report dated Mar. 8, 2017 in International Application No. PCT/KR2016/014282 (2 pages in English).

SEQUENCE LISTING

<160> NUMBER OF SEQ ID NOS: 60

<210> SEQ ID NO 1
<211> LENGTH: 585
<212> TYPE: DNA
<213> ORGANISM: Corynebacterium glutamicum

<400> SEQUENCE: 1

```
atgctctcga caataaaaat gatccgtgaa gatctcgcaa acgctcgtga acacgatcca      60
gcagcccgag gcgatttaga aaacgcagtg gtttactccg gactccacgc catctgggca     120
catcgagttg ccaacagctg gtggaaatcc ggtttccgcg gccccgcccg cgtattagcc     180
caattcaccc gattcctcac cggcattgaa attcaccccg gtgccaccat tggtcgtcgc     240 tttttttattg accacggaat gggaatcgtc atcggcgaaa ccgctgaaat cggcgaaggc     300
gtcatgctct accacggcgt caccctcggc ggacaggttc tcacccaaac caagcgccac     360
cccacgctct gcgacaacgt gacagtcggc gcgggcgcaa aaatcttagg tcccatcacc     420
atcggcgaag gctccgcaat tggcgccaat gcagttgtca ccaaagacgt gccggcagaa     480
cacatcgcag tcggaattcc tgcggtagca cgcccacgtg gcaagacaga gaagatcaag     540
ctcgtcgatc cggactatta cattcaccac caccaccacc actaa                     585
```

<210> SEQ ID NO 2
<211> LENGTH: 954
<212> TYPE: DNA
<213> ORGANISM: Corynebacterium glutamicum

<400> SEQUENCE: 2

```
atgggcaatg tgtacaacaa catcaccgaa accatcggcc acaccccact ggtaaagctg      60
aacaagctca ccgaaggcct cgacgcaact gtcctggtca agcttgagtc attcaaccca     120
gcaaactccg tcaaggaccg tatcggtctg gccatcgttg aagatgcaga gaagtccggt     180
gcactgaagc caggcggcac catcgttgaa gcaacctccg gcaacaccgg tatcgcactg     240
gcaatggtcg gcgctgcacg cggatacaac gttgttctca ccatgccgga gaccatgtcc     300
aacgagcgtc gcgttctcct ccgcgcttac ggtgcagaga tcgttcttac cccaggtgca     360
gcaggcatgc agggtgcaaa ggacaaggca gacgaaatcg tcgctgaacg cgaaaacgca     420
gtccttgctc gccagttcga gaacgaggca aacccacgcg tccaccgcga caccaccgcg     480
aaggaaatcc tcgaagacac cgacggcaac gttgatatct tcgttgcaag cttcggcacc     540
ggcggaaccg tcaccggcgt tggccaggtc ctgaaggaaa caacgcaga cgtacaggtc     600 tacaccgtcg agccagaagc gtccccactt ctgaccgctg gcaaggctgg tccacacaag     660
atccagggca tcggcgcaaa cttcatcccc gaggtcctgg accgcaaggt tctcgacgac     720
gtgctgaccg tctccaacga agacgcaatc gcattctccc gcaagctcgc taccgaagag     780
ggcatcctcg gcggtatctc caccggcgca aacatcaagg cagctcttga ccttgcagca     840
aagccagaga acgctggcaa aaccatcgtc accgttgtca ccgacttcgg cgagcgctac     900
gtctccaccg ttctttacga agacatccgc gaccatcatc atcaccacca ctaa           954
```

<210> SEQ ID NO 3
<211> LENGTH: 1185
<212> TYPE: DNA
<213> ORGANISM: Corynebacterium glutamicum

<400> SEQUENCE: 3

```
atgattggct atggtttacc tatgcccaat caggcccact tctctgcgtc ctttgcccgc      60
```

```
ccctctaccc cggctgcaaa gtgcatgcac catatccgcc tcggccagca actcattaga    120
aatgagctgg tcgaggccac aggtctgtcc caaccgactg tcacccgcgc agtcaccgct    180
ttaatgcagg caggtttggt tcgtgaacgc cctgatctca cactctcatc gggccctggt    240
cgtcccaata ttcctctaga actcgctcca agtccatgga ttcatgcagg cgtggcaatc    300
ggcaccaagt cttcctacgt cgctttgttt gataccaagg tcgcaccct tcgtgatgcc     360 atgctggaaa tctcagcagc tgatttagat ccagacactt tcatcgaaca cctcattgct    420
ggtgtcaacc gcctcaccac tggtcttgat ctaccactgg taggtattgg tgttgccacc    480
tcaggaaaag tcaccaacgc aggcgttgtc accgcaagca acttgggctg ggatggcgtt    540
gatatcgctg gccgcctgaa ctaccaattc agcgttccag caaccgtggc atcagcaatt    600
cctgccatcg cagcttctga actgcaggct tccccacttc cccaccctga gcagccaact    660
cccatcacct tgaccttcta cgccgatgac tctgtgggcg cggcctacag caatgatttg    720
ggagtacatg tcattggacc actggctaca actcgtggat caggtttgga tactttgggc    780
atggctgccg aagatgcgct gagcacccaa ggtttcttaa gcagggtttc tgatcagggt    840
atctttgcca acagccttgg tgagctagtc accattgcta aagacaatga aaccgcacgg    900
gaattcctca cgatcgcgc gaccctgctg gctcacactg ccgcagaagc tgccgaaaca    960
gttaagccat ccaccctggt tctctcggga tcggcgtttt ccgaagatcc acaaggtcgg    1020
tcggtgttcg cttcccaatt gaagaaggaa tacgacgcag acattgagct ccggttgatc    1080
cccacccacc gggaaaacgt ccgcgcagca gctcgagcag tcgcacttga tcgactactc    1140
aacgagccac ttactctcgt accccatcat catcatcatc attag                    1185

<210> SEQ ID NO 4
<211> LENGTH: 8211
<212> TYPE: DNA
<213> ORGANISM: Artificial Sequence
<220> FEATURE:
<223> OTHER INFORMATION: pMT-tac

<400> SEQUENCE: 4
cagtttgttg aagattagat gctataattg ttattaaaag gattgaagga tgcttaggaa     60
gacgagttat taatagctga ataagaacgg tgctctccaa atattcttat ttagaaaagc    120
aaatctaaaa ttatctgaaa agggaatgag aatagtgaat ggaccaataa taatgactag    180
agaagaaaga atgaagattg ttcatgaaat taaggaacga atattggata aatatgggga    240
tgatgttaag gctattggtg tttatggctc tcttggtcgt cagactgatg ggccctattc    300
ggatattgag atgatgtgtg tcatgtcaac agaggaagca gagttcagcc atgaatggac    360
aaccggtgag tggaaggtgg aagtgaattt tgatagcgaa gagattctac tagattatgc    420
atctcaggtg gaatcagatt ggccgcttac acatggtcaa tttttctcta ttttgccgat    480
ttatgattca ggtggatact tagagaaagt gtatcaaact gctaaatcgg tagaagccca    540
aacgttccac gatgcgattt gtgcccttat cgtagaagag ctgtttgaat atgcaggcaa    600
atggcgtaat attcgtgtgc aaggaccgac aacatttcta ccatccttga ctgtacaggt    660
agcaatggca ggtgccatgt tgattggtct gcatcatcgc atctgttata cgacgagcgc    720
ttcggtctta actgaagcag ttaagcaatc agatcttcct tcaggttatg accatctgtg    780
ccagttcgta atgtctggtc aactttccga ctctgagaaa cttctggaat cgctagagaa    840
tttctggaat gggattcagg agtggacaga acgacacgga tatatagtgg atgtgtcaaa    900
```

-continued

```
acgcatacca ttttgaacga tgacctctaa taattgttaa tcatgttggt tacgtattta    960
ttaacttctc ctagtattag taattatcat ggctgtcatg gcgcattaac ggaataaagg   1020
gtgtgcttaa atcgggctgc ctcgcgcgtt tcggtgatga cggtgaaaac ctctgacaca   1080
tgcagctccc ggagacggtc acagcttgtc tgtaagcgga tgccgggagc agacaagccc   1140
gtcagggcgc gtcagcgggt gttggcgggt gtcggggcgc agccatgacc cagtcacgta   1200
gcgatagcgg agtgtatact ggcttaacta tgcggcatca gagcagattg tactgagagt   1260
gcaccatatg cggtgtgaaa taccgcacag atgcgtaagg agaaaatacc gcatcaggcg   1320
ctcttccgct tcctcgctca ctgactcgct gcgctcggtc gttcggctgc ggcgagcggt   1380
atcagctcac tcaaaggcgg taatacggtt atccacagaa tcaggggata acgcaggaaa   1440
gaacatgtga gcaaaaggcc agcaaaaggc caggaaccgt aaaaaggccg cgttgctggc   1500
gttttttcat aggctccgcc cccctgacga gcatcacaaa aatcgacgct caagtcagag   1560
gtggcgaaac ccgacaggac tataaagata ccaggcgttt ccccctggaa gctccctcgt   1620
gcgctctcct gttccgaccc tgccgcttac cggatacctg tccgcctttc tcccttcggg   1680
aagcgtggcg ctttctcata gctcacgctg taggtatctc agttcggtgt aggtcgttcg   1740
ctccaagctg ggctgtgtgc acgaacccccc gttcagccc gaccgctgcg ccttatccgg   1800
taactatcgt cttgagtcca acccggtaag acacgactta tcgccactgg cagcagccac   1860
tggtaacagg attagcagag cgaggtatgt aggcggtgct acagagttct tgaagtggtg   1920
gcctaactac ggctacacta aaggacagt atttggtatc tgcgctctgc tgaagccagt   1980
taccttcgga aaaagagttg gtagctcttg atccggcaaa caaccaccg ctggtagcgg   2040
tggttttttt gtttgcaagc agcagattac gcgcagaaaa aaaggatctc aagaagatcc   2100
tttgatcttt tctacggggt ctgacgctca gtggaacgaa aactcacgtt aagggatttt   2160
ggtcatgaga ttatcaaaaa ggatcttcac ctagatcctt ttaaattaaa aatgaagttt   2220
taaatcaatc taaagtatat atgagtaaac ttggtctgac agttaccaat gcttaatcag   2280
tgaggcacct atctcagcga tctgtctatt tcgttcatcc atagttgcct gactccccgt   2340
cgtgtagata actacgatac gggagggctt accatctggc cccagtgctg caatgatacc   2400
gcgagaccca cgctcaccgg ctccagattt atcagcaata accagccag ccggaagggc   2460
cgagcgcaga gtggtcctg caactttatc cgcctccatc cagtctatta attgttgccg   2520
ggaagctaga gtaagtagtt cgccagttaa tagtttgcgc aacgttgttg ccattgctgc   2580
aggcatcgtg gtgtcacgct cgtcgtttgg tatggcttca ttcagctccg gttcccaacg   2640
atcaaggcga gttacatgat cccccatgtt gtgcaaaaaa gcggttagct ccttcggtcc   2700
tccgatcgtt gtcagaagta agttggccgc agtgttatca ctcatggtta tggcagcact   2760
gcataattct cttactgtca tgccatccgt aagatgcttt tctgtgactg gtgagtactc   2820
aaccaagtca ttctgagaat agtgtatgcg cgaccgagt tgctcttgcc cggcgtcaac   2880
acgggataat accgcgccac atagcagaac tttaaaagtg ctcatcattg gaaaacgttc   2940
ttcggggcga aaactctcaa ggatcttacc gctgttgaga tccagttcga tgtaacccac   3000
tcgtgcaccc aactgatctt cagcatcttt tactttcacc agcgtttctg gtgagcaaa    3060
aacaggaagg caaaatgccg caaaaaaggg aataagggcg acacggaaat gttgaatact   3120
catactcttc cttttcaat attattgaag catttatcag ggttattgtc tcatgagcgg   3180
atacatattt gaatgtattt agaaaaataa acaaataggg gttccgcgca catttccccg   3240
aaaagtgcca cctgatcgtc cattccgaca gcatcgccag tcactatggc gtgctgctag   3300
```

```
cgctatatgc gttgatgcaa tttctatgcg cacccgttct cggagcactg tccgaccgct    3360
ttggccgccg cccagtcctg ctcgcttcgc tacttggagc cactatcgac tacgcgatca    3420
tggcgaccac acccgtcctg tggatcgccg tagagcgatt gaagaccgtc aaccaaaggg    3480
gaagcctcca atcgacgcga cgcgcgctct acggcgatcc tgacgcagat ttttagctat    3540
ctgtcgcagc gccctcaggg acaagccacc cgcacaacgt cgcgagggcg atcagcgacg    3600
ccgcagtact gatcaagtcg gtcaagccaa gcgcaaccag cggcaccgcc gcgagcaacg    3660
tcgcaagggc gatcagggga cgattttttgc gaagaatttc cacggtaaga atccaatctc    3720
tcgaatttag ggtgaaagaa gcttggcata ggggtgtgca cgaactcggt ggaggaaatt    3780
tccgcggggc aaggcttcgc gaagcggagt cgcggcagtg gctttgaaga tctttgggag    3840
cagtccttgt gcgcttacga ggtgagccgg tggggaaccg ttatctgcct atggtgtgag    3900
cccccctaga gagcttcaag agcaatcagc ccgacctaga aaggaggcca agagagagac    3960
ccctacgggg ggaaccgttt tctgcctacg agatggcaca tttactggga agctttacgg    4020
cgtcctcgtg gaagttcaat gcccgcagac ttaagtgctc tattcacggt ctgacgtgac    4080
acgctaaatt cagacatagc ttcattgatt gtcggccacg agccagtctc tccctcaaca    4140
gtcataaacc aacctgcaat ggtcaagcga tttcctttag ctttcctagc ttgtcgttga    4200
ctggacttag ctagtttttc tcgctgtgct cgggcgtact cactgtttgg gtctttccag    4260
cgttctgcgg ccttttttacc gccacgtctt cccatagtgg ccagagcttt tcgccctcgg    4320
ctgctctgcg tctctgtctg acgagcaggg acgactggct ggcctttagc gacgtagccg    4380
cgcacacgtc gcgccatcgt ctggcggtca cgcatcggcg gcagatcagg ctcacggccg    4440
tctgctccga ccgcctgagc gacggtgtag gcacgctcgt aggcgtcgat gatcttggtg    4500 tctttttaggc gctcaccagc cgcttttaac tggtatccca cagtcaaagc gtggcgaaaa    4560
gccgtctcat cacgggcggc acgccctgga gcagtccaga ggacacggac gccgtcgatc    4620
agctctccag acgcttcagc ggcgctcggc aggcttgctt caagcgtggc aagtgctttt    4680
gcttccgcag tggcttttct tgccgcttcg atacgtgccc gtccgctaga aaactcctgc    4740
tcatagcgtt ttttaggttt ttctgtgcct gagatcatgc gagcaacctc cataagatca    4800
gctaggcgat ccacgcgatt gtgctgggca tgccagcggt acgcggtggg atcgtcggag    4860
acgtgcagtg gccaccggct cagcctatgt gaaaaagcct ggtcagcgcc gaaaacgcgg    4920
gtcatttcct cggtcgttgc agccagcagg cgcatattcg ggctgctcat gcctgctgcg    4980
gcatacaccg gatcaatgag ccagatgagc tggcatttcc cgctcagtgg attcacgccg    5040
atccaagctg gcgcttttc caggcgtgcc cagcgctcca aaatcgcgta gacctcgggg    5100
tttacgtgct cgattttccc gccggcctgg tggctcggca catcaatgtc caggacaagc    5160
acggctgcgt gctgcgcgtg cgtcagagca acatactggc accgggcaag cgatttgaa    5220 ccaactcggt ataacttcgg ctgtgtttct cccgtgtccg ggtctttgat ccaagcgctg    5280
gcgaagtcgc gggtcttgct gccctggaaa ttttctctgc ccaggtgagc gaggaattcg    5340
cggcggtctt cgctcgtcca gccacgtgat cgcagcgcga gctcgggatg ggtgtcgaac    5400
agatcagcgg aaaatttcca ggccggtgtg tcaatgtctc gtgaatccgc tagagtcatt    5460
tttgagcgct ttctcccagg tttggactgg gggttagccg acgccctgtg agttaccgct    5520
cacggggcgt tcaacatttt tcaggtattc gtgcagctta tcgcttcttg ccgcctgtgc    5580 gcttttttcga cgcgcgacgc tgctgccgat tcggtgcagg tggtggcggc gctgacacgt    5640
```

```
cctgggcggc cacggccaca cgaaacgcgg catttacgat gtttgtcatg cctgcgggca    5700
ccgcgccacg atcgcggata attctcgctg ccgcttccag ctctgtgacg accatggcca    5760
aaatttcgct cggggacgc acttccagcg ccatttgcga cctagccgcc tccagctcct    5820
cggcgtggcg tttgttggcg cgctcgcggc tggctgcggc acgacacgca tctgagcaat    5880
attttgcgcg ccgtcctcgc gggtcaggcc ggggaggaat caggccaccg cagtaggcgc    5940
aactgattcg atcctccact actgtgcgtc tcctggcgc tgccgagcac gcagctcgtc    6000
agccagctcc tcaagatccg ccacgagagt ttctaggtcg ctcgcggcac tggcccagtc    6060
tcgtgatgct ggcgcgtccg tcgtatcgag agctcgaaaa atccgatca ccgttttaa    6120 atcgacggca gcatcgagcg cgtcggactc cagcgcgaca tcagagagat ccatagctga    6180
tgattcgggc caattttggt acttcgtcgt gaaggtcatg acaccattat aacgaacgtt    6240
cgttaaagtt tttggcggaa atcacgcgg cacgaaaatt ttcacgaagc gggactttgc    6300
gcagctcagg ggtgctaaaa attttgtatc gcacttgatt ttccgaaaga cagatatctg    6360
caaacggtgt gtcgtattct ggcttggttt taaaaatctg gaatcgaaat tgcggggcga    6420
ccgagaagtt tttacaaaag gcaaaaactt ttcgggatct cgagagcctg gggtgcctaa    6480
tgagtgagct aacttacatt aattgcgttg cgctcactgc ccgctttcca gtcgggaaac    6540
ctgtcgtgcc agctgcatta tgaatcggc caacgcgcgg ggagaggcgg tttgcgtatt    6600
gggcgccagt gtggttttc ttttcaccag tgagacgggc aacagctgat tgcccttcac    6660
cgcctggccc tgagagagtt gcagcaagcg gtccacgctg gtttgcccca gcaggcgaaa    6720
atcctgtttg atggtggtta acggcgggat ataacatgag ctgtcttcgg tatcgtcgta    6780
tcccactacc gagatatccg caccaacgcg cagcccggac tcggtaatgg cgcgcattgc    6840
gcccagcgcc atctgatcgt tggcaaccag catcgcagtg gaacgatgc cctcattcag    6900 catttgcatg gtttgttgaa accggacat ggcactccag tcgccttccc gttccgctat    6960
cggctgaatt tgattgcgag tgagatattt atgccagcca gcagacgca gacgcgccga    7020 gacagaactt aatgggcccg ctaacagcgc gatttgctgg tgacccaatg cgaccagatg    7080
ctccacgccc agtcgcgtac cgtcttcatg ggagaaaata atactgttga tgggtgtctg    7140
gtcagagaca tcaagaaata acgccggaac attagtgcag gcagcttcca cagcaatggc    7200
atcctggtca tccagcggat agttaatgat cagcccactg acgcgttgcg cgagaagatt    7260
gtgcaccgcc gctttacagg cttcgacgcc gcttcgttct accatcgaca ccaccacgct    7320
ggcacccagt tgatcggcgc gagatttaat cgccgcgaca atttgcgacg gcgcgtgcag    7380
ggccagactg gaggtggcaa cgccaatcag caacgactgt ttgcccgcca gttgttgtgc    7440
cacgcggttg ggaatgtaat tcagctccgc catcgccgct tccactttt ccgcgtttt    7500 cgcagaaacg tggctggcct ggttcaccac gcgggaaacg gtctgataag agacaccggc    7560
atactctgcg acatcgtata acgttactgg tttcacattc accaccctga attgactctc    7620
ttccgggcgc tatcatgcca taccgcgaaa ggttttgcac cattccatgg tgtcttgaca    7680
attaatcatc ggctcgtata atgtgtggaa ttgtgagcgg ataacaattt cacacaggag    7740
atatcatatc gatggatccc gggtaccgcg gccgctgtt ttggcggatg agagaagatt    7800
ttcagcctga tacagattaa atcagaacgc agaagcggtc tgataaaaca gaatttgcct    7860
ggcggcagta gcgcggtggt cccacctgac cccatgccga actcagaagt gaaacgccgt    7920
agcgccgatg gtagtgtggg gtctccccat gcgagagtag ggaactgcca ggcatcaaat    7980
aaaacgaaag gctcagtcga aagactgggc ctttcgtttt atctgttgtt tgtcggtgaa    8040
```

```
cgctctcctg agtaggacaa atccgccggg agcggatttg aacgttgcga agcaacggcc    8100
cggagggtgg cgggcaggac gcccgccata aactgccagg catcaaatta agcagaaggc    8160
catcctgacg gatggccttt ttgcgtttct acaaactctt ctagagtcga c             8211
```

<210> SEQ ID NO 5
<211> LENGTH: 47
<212> TYPE: DNA
<213> ORGANISM: Artificial Sequence
<220> FEATURE:
<223> OTHER INFORMATION: primer

<400> SEQUENCE: 5

```
ccattccatg gtgtcttgac aattaatcat cggctcgtat aatgtgt                   47
```

<210> SEQ ID NO 6
<211> LENGTH: 39
<212> TYPE: DNA
<213> ORGANISM: Artificial Sequence
<220> FEATURE:
<223> OTHER INFORMATION: primer

<400> SEQUENCE: 6

```
gggatcgata tgatatctcc tgtgtgaaat tgttatccg                            39
```

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7

```
gggctcgaga gcctggggtg cctaatgag                                       29
```

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8

```
gacaccatgg aatggtgcaa aacc                                            24
```

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9

```
gcgcgcggat ccatgctctc gacaataaaa atgatc                               36
```

<210> SEQ ID NO 10
<211> LENGTH: 49
<212> TYPE: DNA
<213> ORGANISM: Artificial Sequence
<220> FEATURE:
<223> OTHER INFORMATION: primer

<400> SEQUENCE: 10

```
caggtacctt agtggtggtg gtggtggtga atgtaatagt ccggatcga                 49
```

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
gcgcggatcc atgggcaatg tgtacaacaa                                   30

<210> SEQ ID NO 12
<211> LENGTH: 49
<212> TYPE: DNA
<213> ORGANISM: Artificial Sequence
<220> FEATURE:
<223> OTHER INFORMATION: primer

<400> SEQUENCE: 12
cagaggtacc ttagtggtgg tgatgatgat ggtcgcggat gtcttcgta              49

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
gcgcgcggat ccatgattgg ctatggttta cc                                32

<210> SEQ ID NO 14
<211> LENGTH: 48
<212> TYPE: DNA
<213> ORGANISM: Artificial Sequence
<220> FEATURE:
<223> OTHER INFORMATION: primer

<400> SEQUENCE: 14
cgcggtaccc taatgatgat gatgatgatg gggtacgaga gtaagtgg               48

<210> SEQ ID NO 15
<211> LENGTH: 49
<212> TYPE: DNA
<213> ORGANISM: Artificial Sequence
<220> FEATURE:
<223> OTHER INFORMATION: primer

<400> SEQUENCE: 15
ctaaaaggag atatagatgg gcaatgtgta caacaacatc accgaaacc              49

<210> SEQ ID NO 16
<211> LENGTH: 49
<212> TYPE: DNA
<213> ORGANISM: Artificial Sequence
<220> FEATURE:
<223> OTHER INFORMATION: primer

<400> SEQUENCE: 16
catctatatc tccttttagt ggtggtggtg gtggtgaatg taatagtcc              49

<210> SEQ ID NO 17
<211> LENGTH: 49
<212> TYPE: DNA
<213> ORGANISM: Artificial Sequence
<220> FEATURE:
<223> OTHER INFORMATION: primer -continued

<400> SEQUENCE: 17
aaaaggagat atagatgatt ggctatggtt tacctatgcc caatcaggc         49

<210> SEQ ID NO 18
<211> LENGTH: 49
<212> TYPE: DNA
<213> ORGANISM: Artificial Sequence
<220> FEATURE:
<223> OTHER INFORMATION: primer

<400> SEQUENCE: 18
catctatatc tcctttagt ggtggtggtg gtggtgaatg taatagtcc          49

<210> SEQ ID NO 19
<211> LENGTH: 49
<212> TYPE: DNA
<213> ORGANISM: Artificial Sequence
<220> FEATURE:
<223> OTHER INFORMATION: primer

<400> SEQUENCE: 19
aaaaggagat atagatgatt ggctatggtt tacctatgcc caatcaggc         49

<210> SEQ ID NO 20
<211> LENGTH: 49
<212> TYPE: DNA
<213> ORGANISM: Artificial Sequence
<220> FEATURE:
<223> OTHER INFORMATION: primer

<400> SEQUENCE: 20
gccaatcatc tatatctcct tttagtggtg gtgatgatga tggtcgcgg         49

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
aatcctcgaa gacaccgacg gcaac                                   25

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
gttgccgtcg gtgtcttcga ggatt                                   25

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gtaatcgcag atcagcaacg c                                       21

<210> SEQ ID NO 24

```
<211> LENGTH: 20
<212> TYPE: DNA
<213> ORGANISM: Artificial Sequence
<220> FEATURE:
<223> OTHER INFORMATION: primer

<400> SEQUENCE: 24
agaaaggagg tgatccagcc                                              20

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
gttgtcgacc ccgaagcc                                                18

<210> SEQ ID NO 26
<211> LENGTH: 23
<212> TYPE: DNA
<213> ORGANISM: Artificial Sequence
<220> FEATURE:
<223> OTHER INFORMATION: primer

<400> SEQUENCE: 26
cacaaatgcc aacggatctt gac                                          23

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
ttgaagctcc aaagcaccag g                                            21

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gacaattgct ggagcttcgc                                              20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gcgttgaagg tttccaggtt c                                            21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
```
caccaaatct tcctcagcgg 20

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
actgcccata ctgcgcgg 18

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
gttgcgactc acctcttttg tgt 23

<210> SEQ ID NO 33
<211> LENGTH: 24
<212> TYPE: DNA
<213> ORGANISM: Artificial Sequence
<220> FEATURE:
<223> OTHER INFORMATION: primer

<400> SEQUENCE: 33
ctccaattat cacctggtca ttgg 24

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
gagtgaagtc cgcattctgt ct 22

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
aggagatcgt caccaagact g 21

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
gaagtagcct tccttcttgc g 21

<210> SEQ ID NO 37
<211> LENGTH: 21
<212> TYPE: DNA

```
<213> ORGANISM: Artificial Sequence
<220> FEATURE:
<223> OTHER INFORMATION: primer

<400> SEQUENCE: 37
tcaacgacaa cgaagcacca g                                              21

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
gatcgaccag ttattgcgta gg                                             22

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
aacacaaggc cgtccacatc                                                20

<210> SEQ ID NO 40
<211> LENGTH: 18
<212> TYPE: DNA
<213> ORGANISM: Artificial Sequence
<220> FEATURE:
<223> OTHER INFORMATION: primer

<400> SEQUENCE: 40
gcagcgtggt aacgggct                                                  18

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
gtcacactga acctgccaaa g                                              21

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ccctttggtt cggagacaac                                                20

<210> SEQ ID NO 43
<211> LENGTH: 18
<212> TYPE: DNA
<213> ORGANISM: Artificial Sequence
<220> FEATURE:
<223> OTHER INFORMATION: primer

<400> SEQUENCE: 43
acagcccttg tgggctcg                                                  18
```

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
cccaacaggt tccaaaactc gt                                        22

<210> SEQ ID NO 45
<211> LENGTH: 18
<212> TYPE: DNA
<213> ORGANISM: Artificial Sequence
<220> FEATURE:
<223> OTHER INFORMATION: primer

<400> SEQUENCE: 45
ccgcctggct ctcactga                                             18

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
gtagcggaag gtgtgacgtt c                                         21

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
acacccgaaa cttgggagtt c                                         21

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
ggcaggtgtg gtgatttcga                                           20

<210> SEQ ID NO 49
<211> LENGTH: 23
<212> TYPE: DNA
<213> ORGANISM: Artificial Sequence
<220> FEATURE:
<223> OTHER INFORMATION: primer

<400> SEQUENCE: 49
atgaatgggc gacgattttc agc                                       23

<210> SEQ ID NO 50
<211> LENGTH: 20
<212> TYPE: DNA
<213> ORGANISM: Artificial Sequence
<220> FEATURE:

<223> OTHER INFORMATION: primer

<400> SEQUENCE: 50
gccctcaaat cgggtgtcta                    20

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
gctttgaaaa ccttgggtgg g                  21

<210> SEQ ID NO 52
<211> LENGTH: 18
<212> TYPE: DNA
<213> ORGANISM: Artificial Sequence
<220> FEATURE:
<223> OTHER INFORMATION: primer

<400> SEQUENCE: 52
gcgaggacac ctgtgagc                      18

<210> SEQ ID NO 53
<211> LENGTH: 23
<212> TYPE: DNA
<213> ORGANISM: Artificial Sequence
<220> FEATURE:
<223> OTHER INFORMATION: primer

<400> SEQUENCE: 53
gtgcctgagc tgcaaaaact tag                23

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
gagtgggctc cctgggaa                      18

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
aactggatct tgtcgtcgat aagg               24

<210> SEQ ID NO 56
<211> LENGTH: 23
<212> TYPE: DNA
<213> ORGANISM: Artificial Sequence
<220> FEATURE:
<223> OTHER INFORMATION: primer

<400> SEQUENCE: 56
gacaaggatc cgatcgtgta ttg                23

```
<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
ccaacgtttt cgatgcggtg                                               20

<210> SEQ ID NO 58
<211> LENGTH: 18
<212> TYPE: DNA
<213> ORGANISM: Artificial Sequence
<220> FEATURE:
<223> OTHER INFORMATION: primer

<400> SEQUENCE: 58
gctgcttagg ctcaccgg                                                 18

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
ctatgagcaa gtcgcgcaag                                               20

<210> SEQ ID NO 60
<211> LENGTH: 23
<212> TYPE: DNA
<213> ORGANISM: Artificial Sequence
<220> FEATURE:
<223> OTHER INFORMATION: primer

<400> SEQUENCE: 60
ctggaaataa acggagtcgc tac                                           23
```

MUTANT MICROORGANISM FOR PRODUCING L-CYSTEINE AND METHOD FOR PRODUCING L-CYSTEINE USING SAME

CROSS REFERENCE TO RELATED APPLICATION(S)

This application is a U.S. national stage application of International Application No. PCT/KR2016/014282 filed on Dec. 7, 2016, which claims the benefit of Korean Patent Application No. 10-2016-0005378 filed on Jan. 15, 2016, in the Korean Intellectual Property Office, the entire disclosures of which are incorporated herein by reference for all purposes.

TECHNICAL FIELD

The present invention relates to an L-cysteine-producing mutant microorganism wherein genes encoding enzymes which are involved in the L-cysteine metabolic pathway are introduced in a microorganism having the ability to produce L-cysteine, and more particularly to an L-cysteine-producing mutant microorganism having introduced therein cysE, cysK and cysR, which are genes encoding enzymes which are involved in the L-cysteine metabolic pathway, and to a method of producing L-cysteine using the mutant microorganism.

BACKGROUND ART

In recent years, the demand for biologically synthesized L-cysteine as a raw material has increased in various industries such as foods, medicines, and cosmetics, and the consumer demand for environmentally friendly biological materials has increased.

L-cysteine is a sulfur-containing non-essential amino acid and has been extracted from human or animal hair by acid hydrolysis and electro-reduction methods. However, industrially, these conventional methods have a problem in that the amount of waste to be disposed and the production cost increase. Socially, these methods cause severe environmental pollution and pose issues related to the use of raw materials of animal origin.

In the current global market, L-cysteine is mostly produced in China and exported overseas. In Korea, the demand for and imports of L-cysteine are increasing, but there is no company that produces L-cysteine.

Due to the absence of L-cysteine production technology in the country, the development of L-cysteine production technology based on environmentally friendly biological materials to replace the Chinese physicochemical treatment method for producing L-cysteine is expected to make it possible to supply L-cysteine as raw material to various industrial field, and the demand for the technology is increasing.

In conventional methods of producing L-cysteine using microorganisms, the synthesis of L-cysteine is limited due to the feedback inhibition regulation present in the amino acid and sulfur metabolic pathways, and thus techniques for biologically producing L-cysteine have limitations such as low productivity (Denk D and Böck A. J. general microbiology (1987) 133:515-525; Nakamori S et al., Appl Environ Microb (1998) 64:1607-1611; Takagi H, Kobayashi C, et al., FEBS Letters (1999) 452:323-327; Takagi H, et al., FEMS microbiology letters (1999) 179:453-459; Wirtz M, et al., Amino acids (2003) 24:195-203; Nakatani T et al., Microbial cell factories (2012) 11:62).

Accordingly, the present inventors have made extensive efforts to develop a technology capable of producing a large amount of L-cysteine by microbial fermentation, and as a result, have found that when an L-cysteine-producing mutant microorganism having introduced therein cysE, cysK and cysR, which are enzymes involved in the L-cysteine metabolic pathway, is used, a sulfur source essential for the synthesis of L-cysteine in the microorganism can be continuously supplied to greatly increase L-cysteine production, thereby completing the present invention.

DISCLOSURE OF INVENTION

Technical Problem

It is an object of the present invention to provide a microorganism having an improved ability to produce L-cysteine.

Another object of the present invention is to provide a method of producing L-cysteine using the mutant microorganism.

Technical Solution

To achieve the above object, the present invention provides an L-cysteine-producing mutant microorganism wherein cysE, cysK and cysR, which are genes encoding enzymes involved in the L-cysteine metabolic pathway, are introduced in a microorganism having the ability to produce L-cysteine.

The present invention also provides a method for producing L-cysteine, comprising the steps of: (a) culturing the mutant microorganism to produce L-cysteine; and (b) recovering the produced L-cysteine.

BEST MODE FOR CARRYING OUT THE INVENTION

Figure 1:
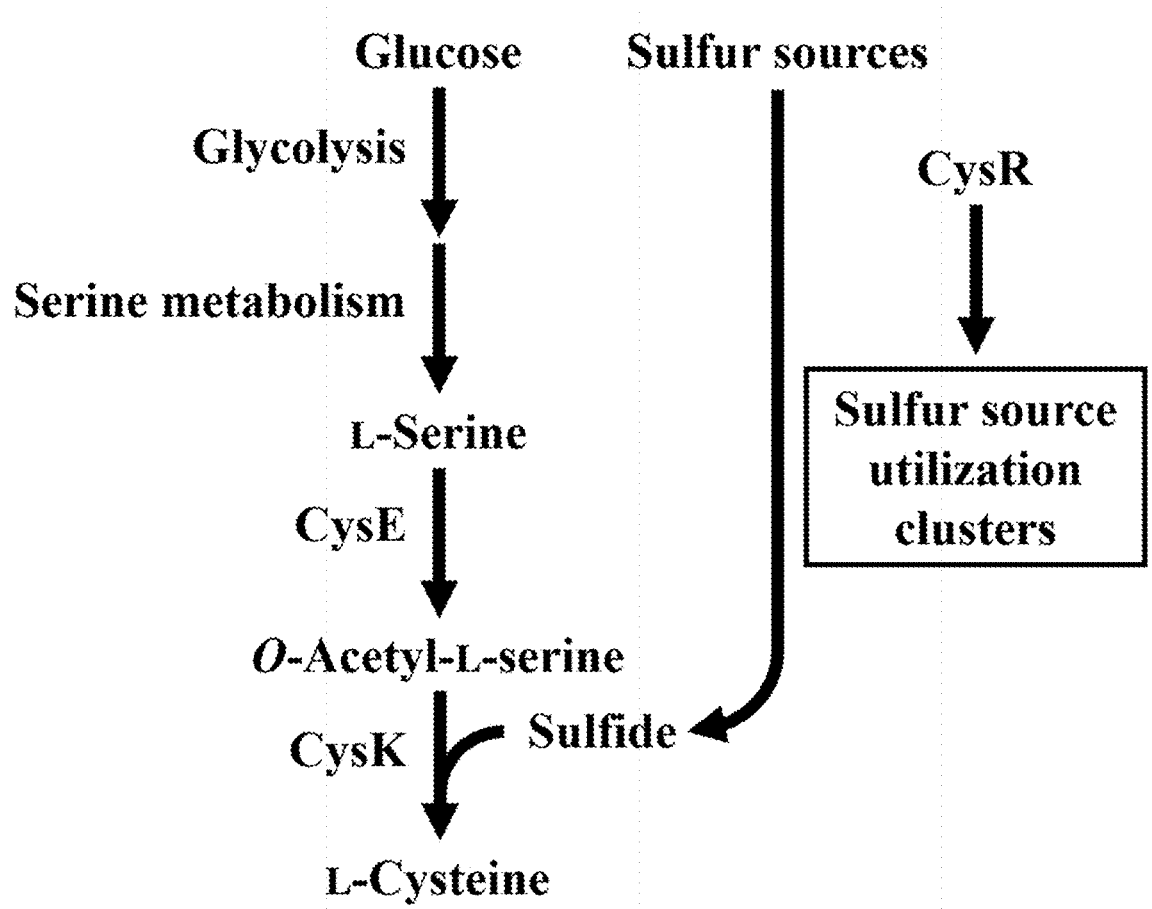
FIG. 1 shows a metabolic pathway related to overexpression for sustainable L-cysteine production in *Corynebacterium glutamicum* and the regulation of a sulfur source absorption system.

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In conventional techniques of producing L-cysteine using microorganisms, the synthesis of L-cysteine is limited due to the feedback inhibition regulation present in the amino acid and sulfur metabolic pathways, and thus techniques for biologically producing L-cysteine have limitations such as low productivity.

In the present invention, in order to remarkably increase the production yield, production rate and productivity of L-cysteine in microbial fermentation, a cysteine metabolic pathway is upregulated by overexpressing L-cysteine synthesis related gene(s) for preventing the feedback inhibition and deregulation in inflow route of sulfur by a transcription activation factor(s).

In one example of the present invention, a transcriptional regulator gene which is derived from a *Corynebacterium glutamicum* strain and activating serine acetyltransferase, acetylserine sulfhydrylase, and sulfur supply gene, was cloned into a vector comprising the tac promoter (which is a hybrid of the lacUV5 promoter and the trp promoter) that induces strong transcription, and then the recombinant vector was introduced into a *Corynebacterium glutamicum* strain, thereby inducing overexpression of each of the enzymes. The highly overexpressed transcriptional regulator (CysR) enabled an external sulfur source to be introduced into the *Corynebacterium glutamicum* strain cells and to be converted into sulfide. Next, the highly overexpressed serine acetyltransferase (CysE) converted intracellular serine, produced by the *Corynebacterium glutamicum* strain, into acetylserine. Next, the highly expressed acetylserine sulfhydrylase (CysK) converted the acetylserine, biosynthesized by the serine acetyltransferase, into L-cysteine.

Therefore, in one aspect, the present invention is directed to an L-cysteine-producing mutant microorganism wherein cysE, cysK and cysR, which are genes encoding enzymes involved in the L-cysteine metabolic pathway, are introduced in a microorganism having the ability to produce L-cysteine.

In the present invention, the cysE may have a nucleotide sequence of SEQ ID NO: 1, the cysK may have a nucleotide sequence of SEQ ID NO: 2, and the cysR may have a nucleotide sequence of SEQ ID NO: 3.

The microorganism having the ability to produce L-cysteine that can be used in the present invention is preferably *Corynebacterium glutamicum*, but is not limited thereto.

It is believed that the L-cysteine-producing mutant microorganism of the present invention will be very advantageously used in processes of producing industrially useful substances such as Co-A, taurine, N-acetylcysteine and methionine which uses L-cysteine as a precursor.

In one example of the present invention, the constructed *Corynebacterium glutamicum* CysEKR was deposited in the Korean Collection for Type Cultures (KCTC), the Korea Research Institute of Bioscience and Biotechnology on Dec. 23, 2015 under accession number KCTC12970BP.

In another aspect, the present invention is directed to a method for producing L-cysteine, comprising the steps of: (a) producing L-cysteine by culturing the mutant microorganism, thereby; and (b) recovering the produced L-cysteine.

Figure 11:
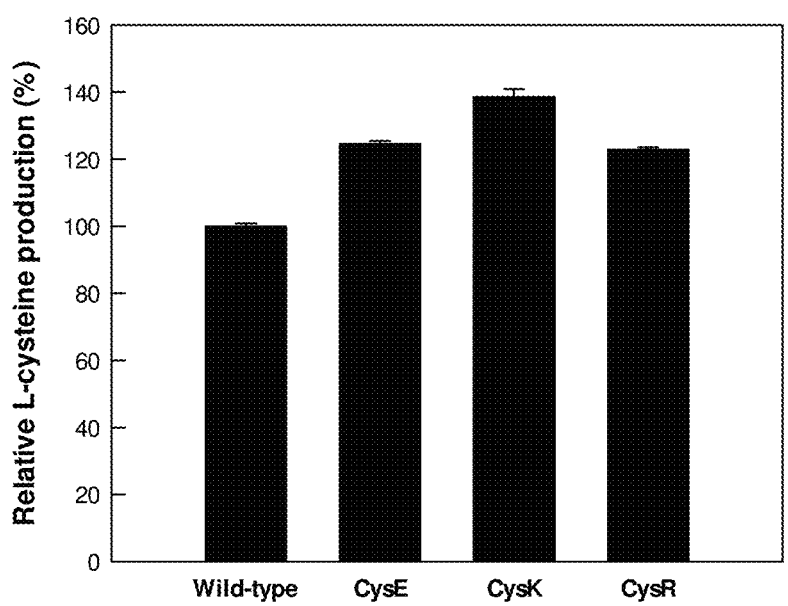
FIG. 11 shows the L-cysteine biosynthetic activities of a wild-type *Corynebacterium glutamicum* strain and single recombinant *Corynebacterium glutamicum* strains (pMT-tac::cysE, pMT-tac::cysK, and pMT-tac::cysR).
Figure 12:
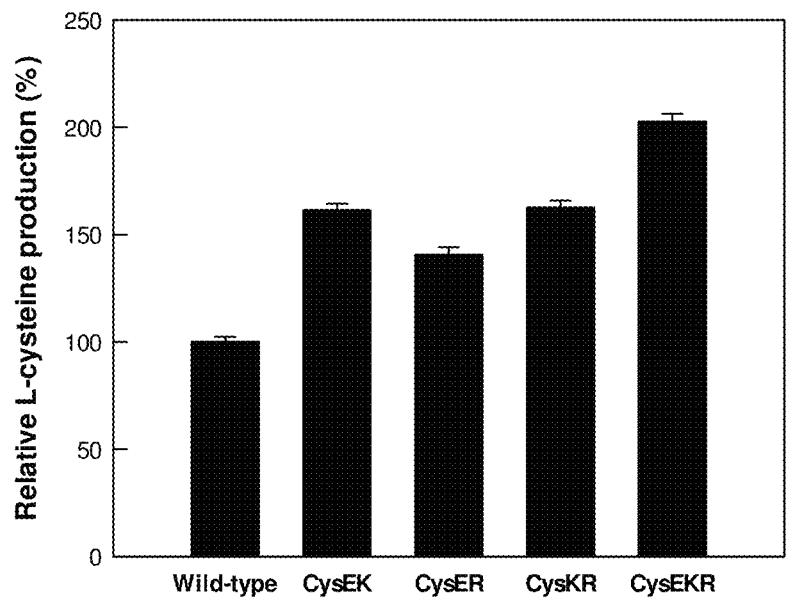
FIG. 12 shows the L-cysteine biosynthetic activities of a wild-type *Corynebacterium glutamicum* strain and dual or triple recombinant *Corynebacterium glutamicum* strains (pMT-tac::cysEK, pMT-tac::cysER, pMT-tac::cysKR, and pMT-tac::cysEKR).

In one example, it was shown that a *Corynebacterium glutamicum* strain having introduced therein the serine acetyltransferase gene, the acetylserine sulfhydrylase gene and the sulfur supply gene group-activating transcriptional regulator gene showed a relatively high ability to produce L-cysteine, compared to a wild-type *Corynebacterium glutamicum* strain and a *Corynebacterium glutamicum* strain having introduced therein one or two of the genes (FIGS. 11 and 12).

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art. Typical expression vectors for mammalian cell culture expression are based on, for example, pRK5 (EP 307,247), pSV16B (WO91/08291), and pVL1392 (Pharmingen).

As used herein, the term "amplifying" or "amplified" is meant to comprehend the mutation, substitution (replacement) or deletion of one or more bases of a target gene, the introduction of one or more bases into the gene, or the introduction of another microbial gene encoding the same enzyme, so as to increase the activity of the corresponding enzyme.

As used herein, the term "expression control sequence" refers to the DNA sequences essential for the expression of the coding sequence operably linked in a particular host organism. Such control sequences include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, any operator sequence, and a ribosomal binding site. Eukaryotic cells include promoters, polyadenylation signals, and enhancers. The factor having the greatest effect on the expression level of the gene in the plasmid is a promoter. SRα promoter, cytomegalovirus promoter and the like are preferably used as a promoter for high expression.

To express the DNA sequence of the present invention, any of a wide variety of expression control sequences may be used in the vector. Examples of useful expression control sequences include, for example, the early and late promoters of SV40 or adenovirus, the lac system, the trp system, the TAC or TRC system, T3 or T7 promoter, the major operator and promoter regions of phage lambda, the control regions of fd coat protein, the promoter for 3-phosphoglycerate kinase or other glycolytic enzymes, a promoter of phosphatase, e.g., Pho5, the promoters of the yeast α-mating system, and other sequences known to control the expression of genes of prokaryotic or eukaryotic cells or their viruses, and various combinations thereof. T7 RNA polymerase promoter Φ10 may be effectively used to express the protein NSP in *E. coli*.

A nucleic acid is "operably linked" when it is placed in a functional relationship with another nucleic acid sequence. The nucleotide sequence may be a gene and a control sequence(s) linked to be capable of expressing the gene when a suitable molecule (e.g., transcription-activating protein) binds to a control sequence(s). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a RBS is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term "expression vector" as used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of host chromosomal DNA once in a host cell, and may produce several copies of the vector and (heterologous) DNA inserted therein.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin. When the expression host is a eukaryotic cell, the expression vector should further include a useful expression marker in a eukaryotic expression cell.

The host cell transformed or transfected by the aforementioned expression vector constitutes another aspect of the present invention. As used herein, the term "transformation" means that DNA can be replicated as a factor outside of chromosome or by means of completion of the entire chromosome by introducing DNA as a host. As used herein, the term "transfection" means that an expression vector is accepted by a host cell regardless of whether or not any coding sequence is actually expressed.

Host cells that are used in the present invention may be prokaryotic cells or eukaryotic cells. In addition, a host is generally used, into which DNA is introduced with high efficiency and in which the introduced DNA is expressed with high efficiency. Examples of host cells that may be used in the present invention include known prokaryotic and eukaryotic hosts such as *E. coli, Pseudomonas* spp., *Bacillus* spp., *Streptomyces* spp., fungi or yeast.

Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden. For example, a vector must be selected considering a host cell, because the vector must be replicated in the host cell. Specifically, the copy number of the vector, the ability of regulating the copy number and the expression of other protein encoded by the corresponding vector (e.g., the expression of an antibiotic marker) should also be considered. Also, an expression control sequence may be selected taking several factors into consideration. For example, relative strength, control capacity and compatibility with the DNA sequence of the present invention of the sequence should be deliberated particularly with respect to possible secondary structures. Further, the selection of a host cell may be made under consideration of compatibility with a selected vector, toxicity of a product encoded by a DNA sequence, secretory nature of the product, ability to correctly fold a polypeptide, fermentation or cultivation requirements, ability to ensure easy purification of a product encoded by a DNA sequence, or the like.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Construction of Recombinant Overexpression Vector for Transformation of *Corynebacterium glutamicum*

Figure 2:
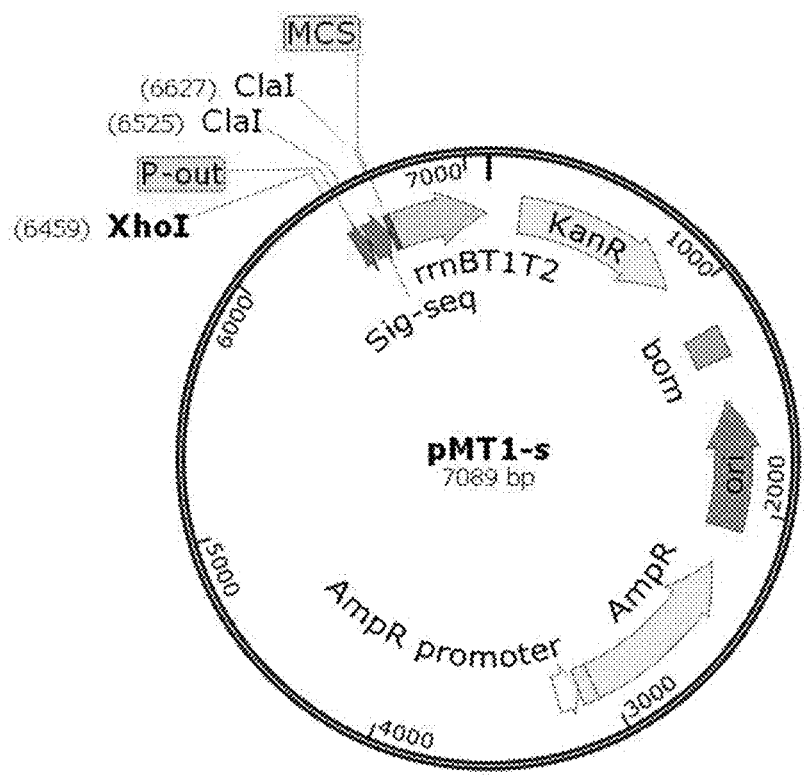
FIG. 2 shows the structure of a recombinant vector (pMT1-s) for constitutive overexpression in *Corynebacterium glutamicum*.
Figure 3:
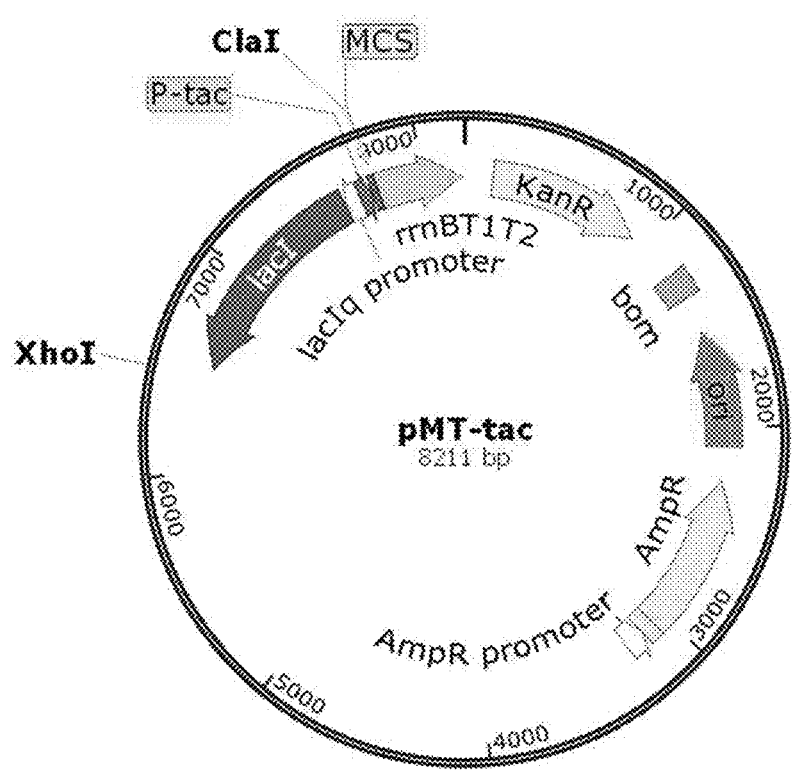
FIG. 3 shows the structure of a recombinant vector (pMT-tac) for overexpression in *Corynebacterium glutamicum*.
Figure 4:
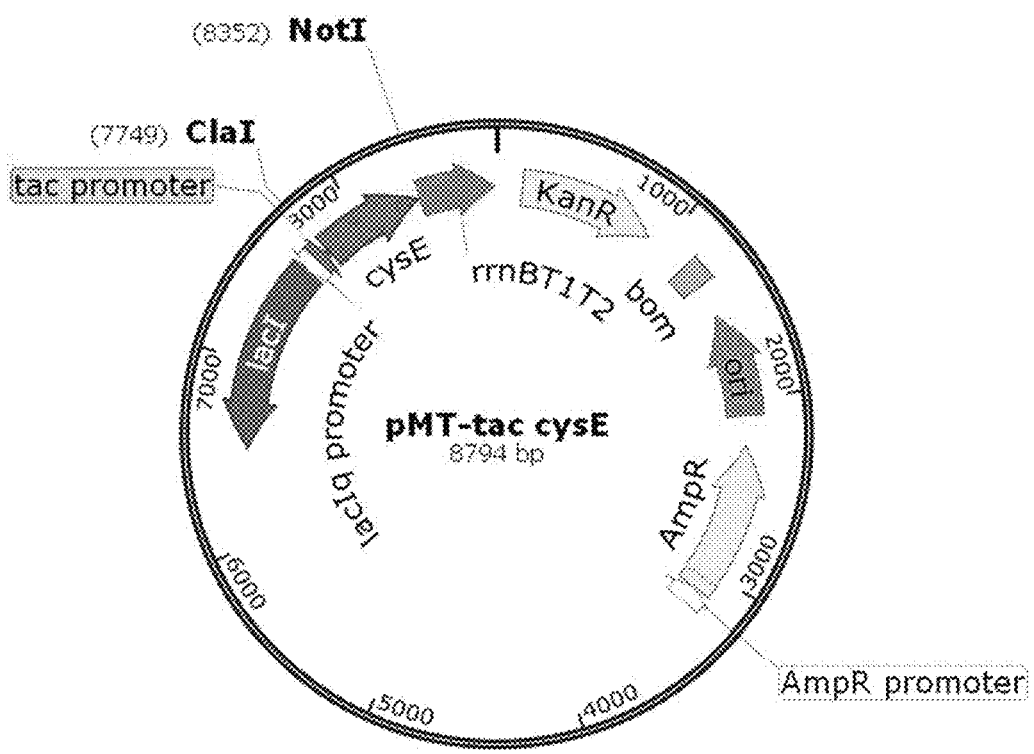
FIG. 4 shows the structure of a recombinant vector (pMT-tac::cysE) for overexpression of CysE in *Corynebacterium glutamicum*.
Figure 5:
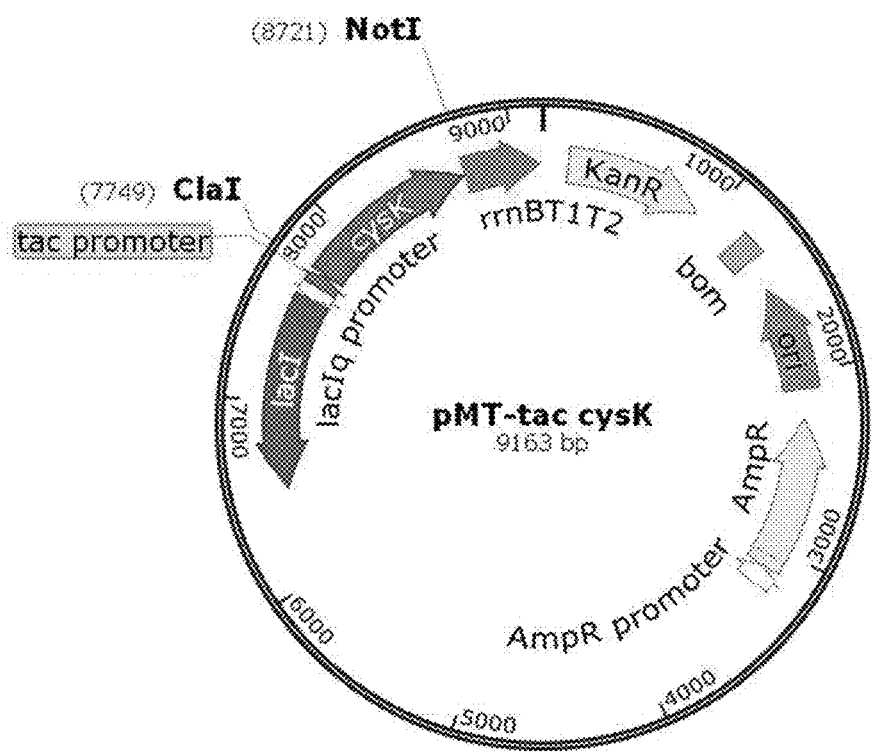
FIG. 5 shows the structure of a recombinant vector (pMT-tac::cysK) for overexpression of CysK in *Corynebacterium glutamicum*.
Figure 6:
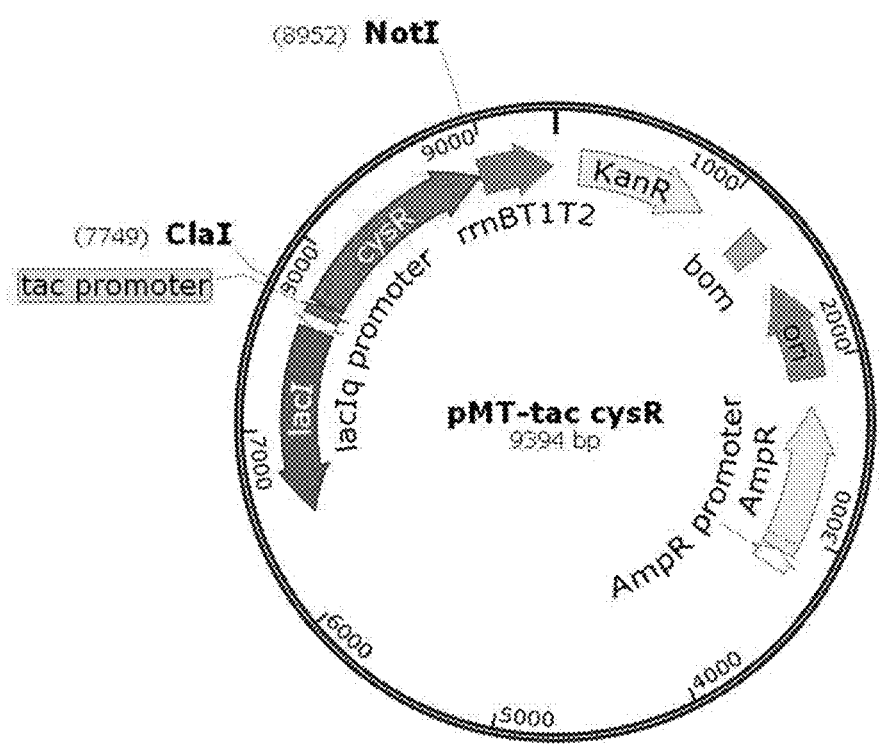
FIG. 6 shows the structure of a recombinant vector (pMT-tac::cysR) for overexpression of CysR in *Corynebacterium glutamicum*.
Figure 7:
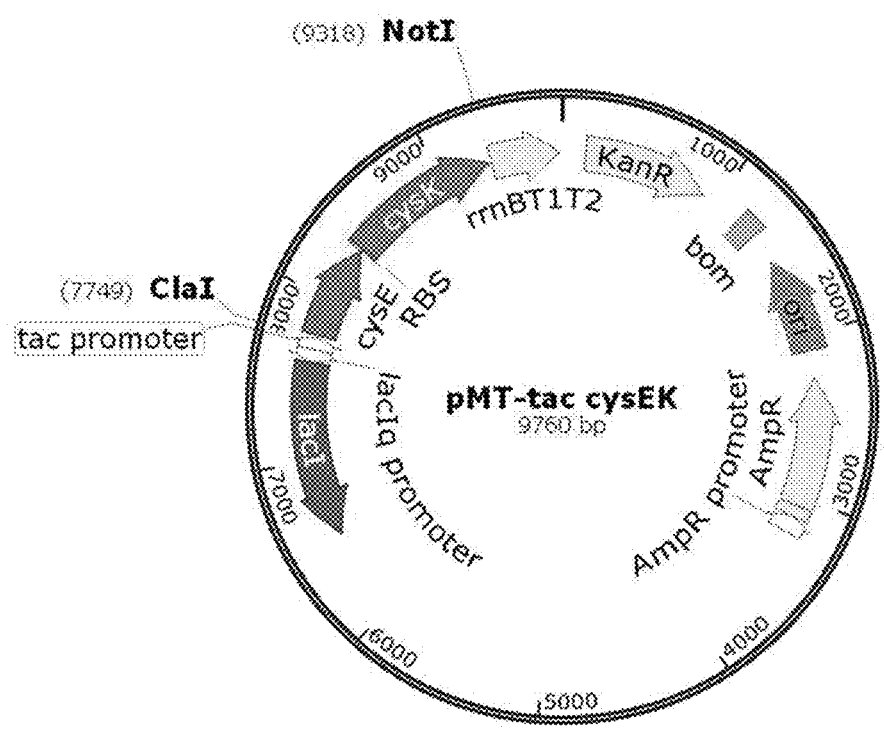
FIG. 7 shows the structure of a recombinant vector (pMT-tac::cysEK) for overexpression of CysEK in *Corynebacterium glutamicum*.
Figure 8:
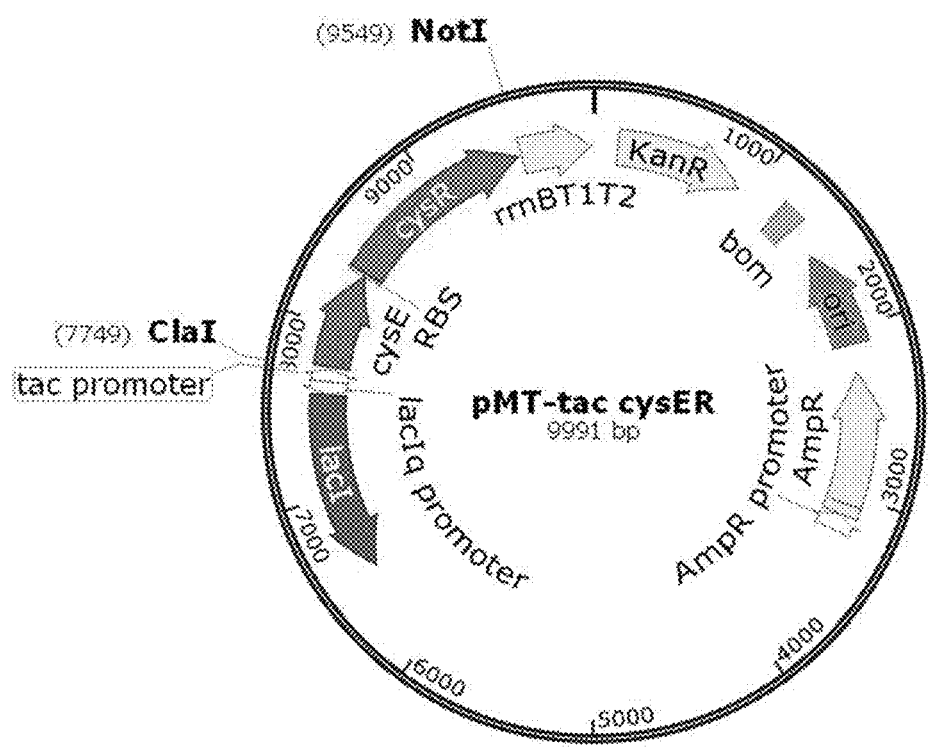
FIG. 8 shows the structure of a recombinant vector (pMT-tac::cysER) for overexpression of CysER in *Corynebacterium glutamicum*.
Figure 9:
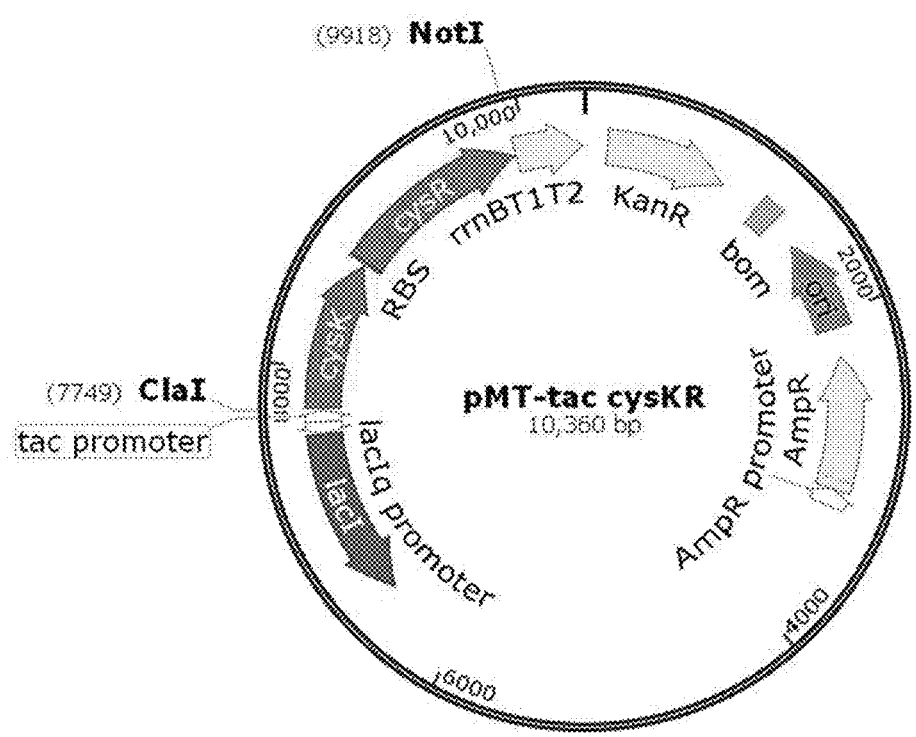
FIG. 9 shows the structure of a recombinant vector (pMT-tac::cysKR) for overexpression of CysKR in *Corynebacterium glutamicum*.
Figure 10:
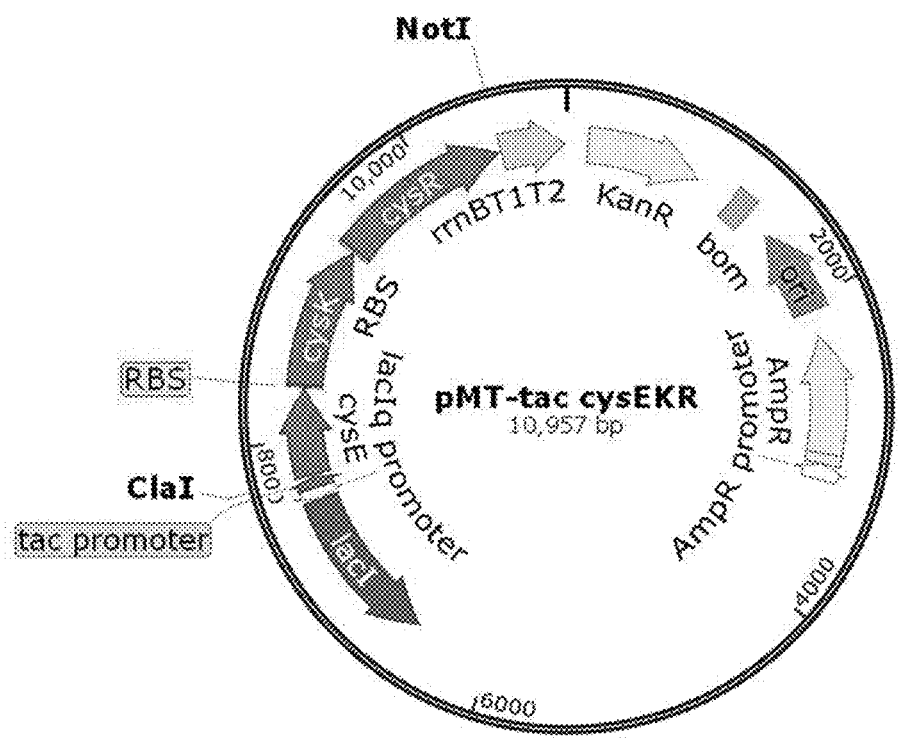
FIG. 10 shows the structure of a recombinant vector (pMT-tac::cysEKR) for overexpression of CysEKR in *Corynebacterium glutamicum*.

In order to remove a constitutively expressing P-out promoter gene and a signal peptide sequence, which promotes extracellular secretion of expression protein, from the recombinant vector pMT-s (FIG. 2) for transformation of *Corynebacterium glutamicum*, the 5' end was digested with the restriction enzyme XhoI, and the 3' end was digested with the restriction enzyme ClaI. The tac promoter gene (which is a highly expressing hybrid promoter gene consisting of a hybrid of the lacUV5 promoter gene and the trp promoter gene) and the lacI gene encoding an expression regulation inhibitor were subjected to PCR and overlap- PCR. The PCR products were ligated to each other, digested with the above-described restriction enzymes, and then inserted into the vector pMT1-s, thereby constructing the recombinant vector pMT-tac (FIG. 3) for overexpression in *Corynebacterium glutamicum*. The nucleotide sequence of pMT-tac is represented by SEQ ID NO: 4.

Example 2: Preparation of *Corynebacterium glutamicum*-Derived Genes Encoding Enzymes Involved in L-Cysteine Metabolic Pathways For cloning serine acetyltransferase (cysE), acetylserine sulfhydrylase (cysK), and sulfur supply gene group-activating transcriptional regulator (cysR) genes, derived from a *Corynebacterium glutamicum* strain, into the recombinant overexpression vector pMT-tac which is constructed in Example 1 for transformation of *Corynebacterium glutamicum*, with reference to the nucleotide sequence of SEQ ID NOs: 1 to 3 for the genes, respectively, primers were synthesized such that a restriction enzyme ClaI recognition sequence was inserted in the 5' end of a forward primer and a restriction enzyme NotI recognition sequence was inserted in the 5' end of a reverse primer.

In order to construct each of serine acetyltransferase-ribosomal binding site-acetylserine sulfhydrylase (cysEK), serine acetyltransferase-ribosomal binding site-sulfur supply gene group activating transcriptional regulator (cysER), acetylserine sulfhydrylase-ribosomal binding site-sulfur supply gene group activating transcriptional regulator (cysKR), and serine acetyltransferase-ribosomal binding site-acetylserine sulfhydrylase-ribosomal binding site-sulfur supply gene group activating transcriptional regulator (cysEKR), forward and reverse primers were synthesized such that a ribosomal binding site sequence was inserted in each linking site. Next, using the synthesized primers, PCR and overlap-PCR were performed. The sequences of the primers used are shown in Table 1 below.

TABLE 1 tac F (SEQ ID NO: 5)
CCATTCCATGGTGTCTTGACAATTAATCATCGGCTCGTATAATGTGT tac R(Cla I) (SEQ ID NO: 6)
GGGATGATATCTCCTGTGTGAAATTGTTATCCG lacI F (Xho I) (SEQ ID NO: 7)
GGG*CTCGAG*AGCCTGGGGTGCCTAATGAG lacI R (SEQ ID NO: 8)
GACACCATGGAATGGTGCAAAACC cysE F(BamHI) (SEQ ID NO: 9)
CGCGC*GGATCC*ATGCTCTCGACAATAAAAATGATC cysE F(KpaI) (SEQ ID NO: 10)
CA*GGTACC*TTAGTGGTGGTGGTGGTGGTGAATGTAATAGTCCGGATCGA cysK F(BamHI) (SEQ ID NO: 11)
GCGC*GGATCC*ATGGGCAATGTGTACAACAA cysK R(KpaI) (SEQ ID NO: 12)
6)CAGA*GGTACC*TTAGTGGTGGTGATGATGATGGTCGCGGATGTCTTCGTA cysR F(BamHI) (SEQ ID NO: 13)
GCGCGC*GGATCC*ATGATTGGCTATGGTTTACC cysR R(KpaI) (SEQ ID NO: 14)
CGC*GGTACC*CTAATGATGATGATGATGATGGGGTACGAGAGTAAGTGG TABLE 1-continued OE cysEK MF (SEQ ID NO: 15)
*CTAA*
<u>AAGGAGATATAG</u>
ATGGGCAATGTGTACAACAACATCACCGAAACC OE cysEK MR (SEQ ID NO: 16)
CATCTATATCTCCTTTTAGTGGTGGTGGTGGTGGTGAATGTAATAGTCC OE cysER MF (SEQ ID NO: 17)
<u>AA</u>
<u>AAGGAGATATAG</u>
ATGATTGGCTATGGTTTACCTATGCCCAATCAGGC OE cysER MR (SEQ ID NO: 18)
CATCTATATCTCCTTTTAGTGGTGGTGGTGGTGGTGAATGTAATAGTCC OE cysKR MF (SEQ ID NO: 19)
<u>AA</u>
<u>AAGGAGATATAG</u>
ATGATTGGCTATGGTTTACCTATGCCCAATCAGGC OE cysKR MR (SEQ ID NO: 20)
GCCAATCATCTATATCTCCTTTTAGTGGTGGTGATGATGATGGTCGCGG OE cysEKR MF (SEQ ID NO: 21)
AATCCTCGAAGACACCGACGGCAAC OE cysEKR MR (SEQ ID NO: 22)
GTTGCCGTCGGTGTCTTCGAGGATT

*Restriction enzyme sites (italic), 5-end nucleotide extension sites (underlined), <u>ribosomalbindingsites(boldandunderlined)</u>

Example 3: Construction of Recombinant Vectors Inserted with Each of cysE, cysK, cysR, cysEK, cysER, cysKR and cysEKR Genes and Transformation of the Vectors into *Corynebacterium glutamicum*

Each of the serine acetyltransferase (cysE), acetylserine sulfhydrylase (cysK), sulfur supply gene group-activating transcriptional regulator (cysR) genes, serine acetyltransferase-ribosomal binding site-acetylserine sulfhydrylase (cysEK), serine acetyltransferase-ribosomal binding site-sulfur supply gene group activating transcriptional regulator (cysER), acetylserine sulfhydrylase-ribosomal binding site-sulfur supply gene group activating transcriptional regulator (cysKR), and serine acetyltransferase-ribosomal binding site-acetylserine sulfhydrylase-ribosomal binding site-sulfur supply gene group activating transcriptional regulator (cysEKR) genes, derived from a *Corynebacterium glutamicum* strain and obtained in Example 2, was electrophoresed on 0.8% agarose gel. The DNA fragments on the agarose gels were recovered using a gel extraction kit (GeneAll).

Next, Each of the serine acetyltransferase (cysE), acetylserine sulfhydrylase (cysK), sulfur supply gene group-activating transcriptional regulator (cysR) genes, serine acetyltransferase-ribosomal binding site-acetylserine sulfhydrylase (cysEK), serine acetyltransferase-ribosomal binding site-sulfur supply gene group activating transcriptional regulator (cysER), acetylserine sulfhydrylase-ribosomal binding site-sulfur supply gene group activating transcriptional regulator (cysKR), and serine acetyltransferase-ribosomal binding site-acetylserine sulfhydrylase-ribosomal binding site-sulfur supply gene group activating transcriptional regulator (cysEKR) genes was digested with the restriction enzyme NotI and the restriction enzyme ClaI, and then was ligated to the recombinant overexpression vector pMT-tac digested with the restriction enzyme NotI and the restriction enzyme ClaI for transformation of *Corynebacterium glutamicum*. The ligation product was transformed into *E. coli* DH5α. Next, the recombinant plasmid DNA was isolated from the transformant. The isolated recombinant plasmid DNA was transformed into *Corynebacterium glutamicum* ATCC 13032.

The recombinant vectors were named pMT-tac::cysE, pMT-tac::cysK, pMT-tac::cysR, pMT-tac::cysEK, pMT-tac::cysER, pMT-tac::cysKR, and pMT-tac::cysEKR, and were shown in FIGS. 4 to 10.

The *Corynebacterium glutamicum* transformants were named *Corynebacterium glutamicum* CysE, *Corynebacterium glutamicum* CysK, *Corynebacterium glutamicum* CysR, *Corynebacterium glutamicum* CysEK, *Corynebacterium glutamicum* CysER, *Corynebacterium glutamicum* CysKR, and *Corynebacterium glutamicum* CysEKR, respectively. *Corynebacterium glutamicum* CysEKR was deposited in the Korean Collection for Type Cultures (KCTC), Korean Research Institute of Bioscience and Biotechnology on Dec. 23, 2015 under accession number KCTC12970BP.

Example 4: Analysis of Cysteine Production in cysE, cysK and cysR Transformants

Cysteine production in the *Corynebacterium glutamicum* CysE, *Corynebacterium glutamicum* CysK and *Corynebacterium glutamicum* CysR transformants, obtained in Example 3, was compared with cysteine production in a wild-type *Corynebacterium glutamicum* strain.

Each of the *Corynebacterium glutamicum* transformant and the wild-type *Corynebacterium glutamicum* strain was cultured in a flask containing a CGXII liquid medium at 30° C. and 200 rpm for 10 hours and the expression of serine acetyltransferase (cysE), acetylserine sulfhydrylase (cysK), and sulfur supply gene group-activating transcriptional regulator (cysR) proteins was induced by IPTG. Next, the culture was collected and centrifuged, and the cells were lysed by the methanol-quenching method. The lysed cells were dried, and then analyzed by HPLC using a Waters AccQ-tag amino acid analysis kit (Waters, USA).

As a result, as can be seen in FIG. 11, L-cysteine was much more produced in the *Corynebacterium glutamicum* CysE, *Corynebacterium glutamicum* CysK or *Corynebacterium glutamicum* CysR transformant than in the wild type.

Example 5: Analysis of Cysteine Production in cysEK, cysER, cysKR and cysEKR Transformants Cysteine production in the *Corynebacterium glutamicum* CysEK, *Corynebacterium glutamicum* CysER, *Corynebacterium glutamicum* CysKR and *Corynebacterium glutamicum* CysEKR transformants, obtained in Example 3, was compared with cysteine production in the wild-type strain.

Each of the *Corynebacterium glutamicum* transformant and the wild-type *Corynebacterium glutamicum* strain was cultured in a flask containing a CGXII liquid medium at 30° C. and 200 rpm for 10 hours and the expression of serine acetyltransferase (cysE), acetylserine sulfhydrylase (cysK), and sulfur supply gene group-activating transcriptional regulator (cysR) proteins was induced by IPTG. Next, the culture was collected and centrifuged, and the cells were lysed by the methanol-quenching method. The lysed cells were dried, and then analyzed by HPLC using a Waters AccQ-tag amino acid analysis kit.

As a result, as can be seen in FIG. 12, the *Corynebacterium glutamicum* CysEK, *Corynebacterium glutamicum* CysER, *Corynebacterium glutamicum* CysKR and *Corynebacterium glutamicum* CysEKR transformants all showed an increased ability to biosynthesize L-cysteine, compared to the wild-type strain. In particular, the CysEKR transformant showed a significantly high ability to biosynthesize L-cysteine, compared to the CysEK, CysER and CysKR transformants.

Example 6: Analysis of Intracellular Sulfur Accumulation of cysR, cysEK, cysER, cysKR and cysEKR Transformants and Wild-Type Strain Intracellular sulfide accumulation in the *Corynebacterium glutamicum* CysR, *Corynebacterium glutamicum* CysEK, *Corynebacterium glutamicum* CysER, *Corynebacterium glutamicum* CysKR and *Corynebacterium glutamicum* CysEKR transformants, obtained in Example 3, was compared with intracellular sulfide accumulation in the wild-type strain.

Each of the *Corynebacterium glutamicum* transformants and the wild-type strain was cultured in a flask containing a CGXII liquid medium at 30° C. and 200 rpm for 10 hours and the expression of serine acetyltransferase (cysE), acetylserine sulfhydrylase (cysK), and sulfur supply gene group-activating transcriptional regulator (cysR) proteins was induced by IPTG. Next, the culture was collected and centrifuged, and only the cells were collected and lysed with 6% (wt/vol) NaOH at 95° C. for 15 minutes. Intracellular sulfur accumulation in the lysed cell sample was determined by methylene blue method and the absorbance measurement with a spectrophotometer.

In order to quantify sulfur, the absorbance at each concentration of the standard sodium sulfate was measured to plot a standard curve, thereby obtaining a linear equation. Next, all sulfur concentrations were quantified by substituting the absorbance into the linear equation.

Figure 13:
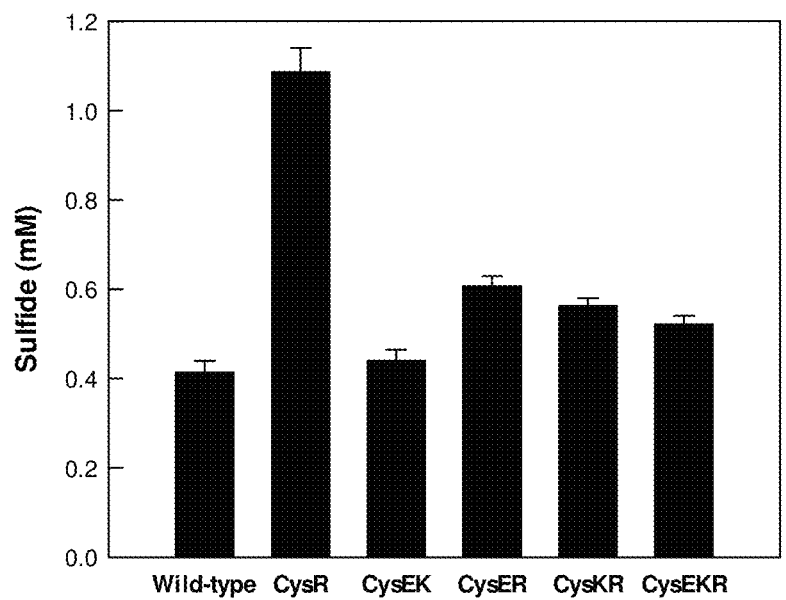
FIG. 13 shows intracellular sulfide accumulation in each of a wild-type *Corynebacterium glutamicum* strain and single, dual or triple recombinant *Corynebacterium glutamicum* strains (pMT-tac::cysR, pMT-tac::cysEK, pMT-tac::cysER, pMT-tac::cysKR, pMT-tac::cysEKR).

As a result, as can be seen in FIG. 13, the intracellular sulfur concentration was the highest in the *Corynebacterium glutamicum* CysR strain.

Example 7: Analysis of Cysteine Production in CysEKR Transformant

Cell growth, glucose consumption and cysteine production in each of the *Corynebacterium glutamicum* CysEKR transformant, obtained in Example 3, and the wild-type *Corynebacterium glutamicum* strain, were analyzed as a function of time.

Each of the *Corynebacterium glutamicum* transformants and the wild-type strain was cultured in a flask containing a CGXII liquid medium at 30° C. and 200 rpm for 15 hours such that the expression of serine acetyltransferase (cysE), acetylserine sulfhydrylase (cysK), and sulfur supply gene group-activating transcriptional regulator (cysR) proteins was induced by IPTG.

Figure 14A:
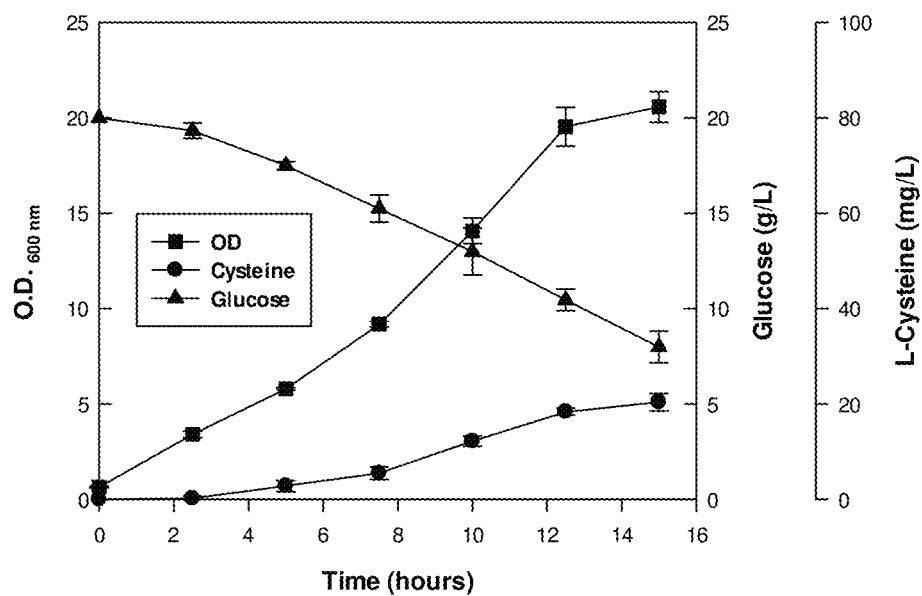
FIG. 14 shows the results of comparing time-dependent L-cysteine production between a wild-type *Corynebacterium glutamicum* strain (FIG. 14A) and a final triple *Corynebacterium glutamicum* strain (pMT-tac::cysEKR) (FIG. 14B).
Figure 14B:
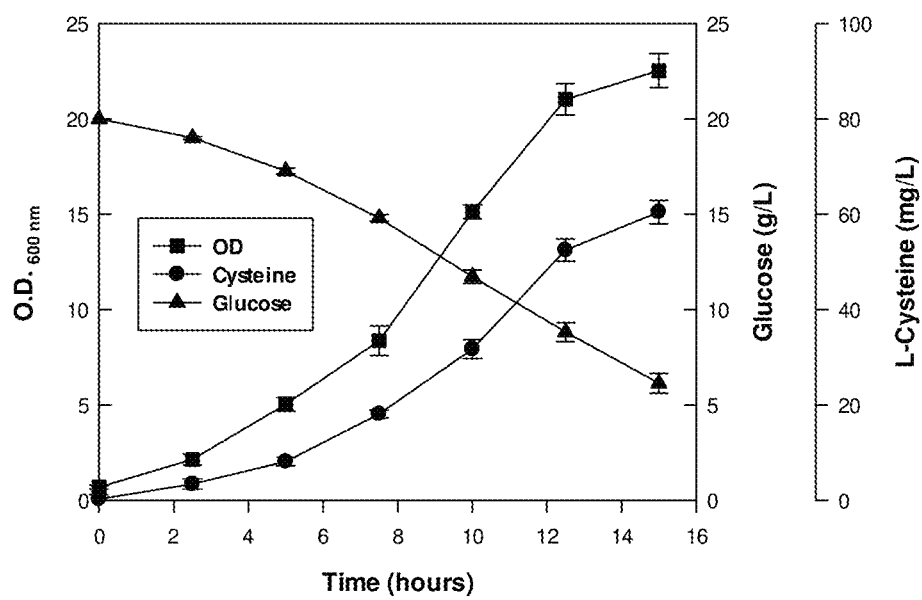

Next, the culture was collected at the indicated time points as shown in FIG. 14, followed by centrifugation, and the supernatant was analyzed by HPLC to measure the amount of glucose. After centrifugation, the collected cells were lysed by the methanol-quenching method. The lysed cell sample was dried, and then analyzed by HPLC using a Waters AccQ-tag amino acid analysis kit. For analysis of cell growth, the culture was collected at the indicated time points as shown in FIG. 14, and the absorbance of the culture was measured with a spectrophotometer. The results are shown in FIG. 14.

Example 8: Analysis of the mRNA Expression Levels of Sulfur Source Supply-Related Genes by CysR Overexpression The mRNA expression levels of sulfur supply-related genes in *Corynebacterium glutamicum* CysR, confirmed in Example 6, were compared with that in the wild-type *Corynebacterium glutamicum* strain.

Each of the wild-type *Corynebacterium glutamicum* strain and the *Corynebacterium glutamicum* CysR strain was cultured in a flask containing a CGXII liquid medium at 30° C. and 200 rpm for 10 hours and the expression of the transcriptional regulator (cysR) protein was induced by IPTG. Next, the culture was collected and centrifuged, and the cells were lysed with Tri-RNA reagent (Favorgen Biotech Corp., Taiwan). The lysed cell sample was centrifuged with chloroform, and the supernatant containing total RNA was collected. The total RNA was purified with isopropyl alcohol and dried, after which mRNA expression levels were analyzed using Reverse Transcription Master Premix (Elpisbio, Korea) and HiPi Real-Time PCR 2× Master Mix (SYBR green) (Elpisbio, Korea) in StepOnePlus thermocycler (Thermo Fisher Scientific, USA). The sequences of the primers used are shown in Table 2 below.

The mRNA levels of the wild-type *Corynebacterium glutamicum* and the *Corynebacterium glutamicum* CysR were normalized using the mRNA levels of the *Corynebacterium glutamicum* 16S rRNA (NCBI Gene ID: 444304238) gene as an internal reference.

Figure 15:
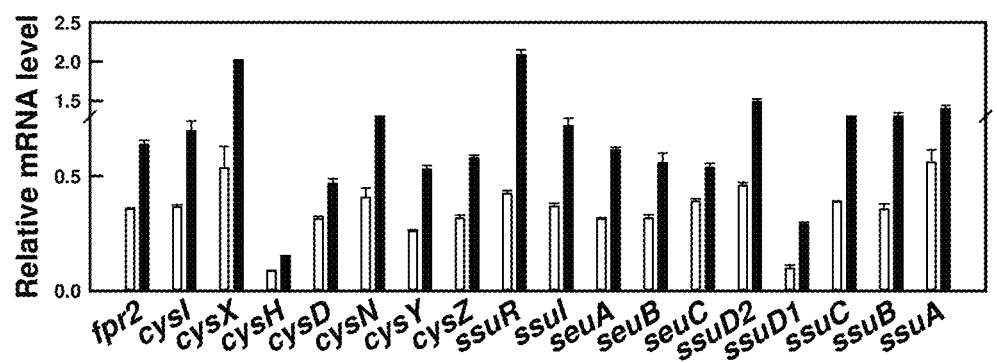
FIG. 15 shows the results of analyzing the mRNA expression levels of sulfur source-related genes in a wild-type *Corynebacterium glutamicum* strain and a *Corynebacterium glutamicum* strain (pMT-tac::cysR) overexpressing the transcriptional regulator CysR.

As a result, as can be seen in FIG. 15, the mRNA expression levels of the sulfur source supply-related gene groups fpr2-cysIXHDNYZ (assimilatory sulfate assimilatory reduction cluster, NCBI Gene ID: 21325585-21325591), ssuR (transcriptional regulator, NCBI Gene ID: 21322774), ssuI-seuABC-ssuD2 and ssuD1CBA (sulfonate and sulfonate ester assimilatory reduction cluster, NCBI Gene ID: 21323778-21323785 and 21323987-21323990)) in the *Corynebacterium glutamicum* CysR transformant all increased compared to those in the wild-type strain. This demonstrates that the transcriptional regulator (cysR) protein actually activates the group of sulfur supply-related genes.

TABLE 2

| Primer Sequences | |
|---|---|
| Primer | Sequence |
| 16S rRNA F (SEQ ID NO: 23) | GTAATCGCAGATCAGCAACGC |
| 16S rRNA R (SEQ ID NO: 24) | AGAAAGGAGGTGATCCAGCC |
| ssuR F (SEQ ID NO: 25) | GTTGTCGACCCCGAAGCC |
| ssuR R (SEQ ID NO: 26) | CACAAATGCCAACGGATCTTGAC |
| fpr2 F (SEQ ID NO: 27) | TTGAAGCTCCAAAGCACCAGG |
| fpr2 R (SEQ ID NO: 28) | GACAATTGCTGGAGCTTCGC |
| cysI F (SEQ ID NO: 29) | GCGTTGAAGGTTTCCAGGTTC |
| cysI R (SEQ ID NO: 30) | CACCAAATCTTCCTCAGCGG |
| cysX F (SEQ ID NO: 31) | ACTGCCCATACTGCGCGG |
| cysX R (SEQ ID NO: 32) | GTTGCGACTCACCTCTTTTGTGT |
| cysH F (SEQ ID NO: 33) | CTCCAATTATCACCTGGTCATTGG |
| cysH R (SEQ ID NO: 34) | GAGTGAAGTCCGCATTCTGTCT |
| cysD F (SEQ ID NO: 35) | AGGAGATCGTCACCAAGACTG |
| cysD R (SEQ ID NO: 36) | GAAGTAGCCTTCCTTCTTGCG |
| cysN F (SEQ ID NO: 37) | TCAACGACAACGAAGCACCAG |

TABLE 2-continued

| Primer Sequences | |
|---|---|
| Primer | Sequence |
| cysN R (SEQ ID NO: 38) | GATCGACCAGTTATTGCGTAGG |
| cysY F (SEQ ID NO: 39) | AACACAAGGCCGTCCACATC |
| cysY R (SEQ ID NO: 40) | GCAGCGTGGTAACGGGCT |
| cysZ F (SEQ ID NO: 41) | GTCACACTGAACCTGCCAAAG |
| cysZ R (SEQ ID NO: 42) | CCCTTTGGTTCGGAGACAAC |
| ssuD1 F (SEQ ID NO: 43) | ACAGCCCTTGTGGGCTCG |
| ssuD1 R (SEQ ID NO: 44) | CCCAACAGGTTCCAAAACTCGT |
| ssuC F (SEQ ID NO: 45) | CCGCCTGGCTCTCACTGA |
| ssuC R (SEQ ID NO: 46) | GTAGCGGAAGGTGTGACGTTC |
| ssuB F (SEQ ID NO: 47) | ACACCCGAAACTTGGGAGTTC |
| ssuB R (SEQ ID NO: 48) | GGCAGGTGTGGTGATTTCGA |
| ssuA F (SEQ ID NO: 49) | ATGAATGGGCGACGATTTTCAGC |
| ssuA R (SEQ ID NO: 50) | GCCCTCAAATCGGGTGTCTA |
| ssuI F (SEQ ID NO: 51) | GCTTTGAAAACCTTGGGTGGG |
| ssuI R (SEQ ID NO: 52) | GCGAGGACACCTGTGAGC |
| seuA F (SEQ ID NO: 53) | GTGCCTGAGCTGCAAAAACTTAG |
| seuA R (SEQ ID NO: 54) | GAGTGGGCTCCCTGGGAA |
| seuB F (SEQ ID NO: 55) | AACTGGATCTTGTCGTCGATAAGG |
| seuB R (SEQ ID NO: 56) | GACAAGGATCCGATCGTGTATTG |
| seuC F (SEQ ID NO: 57) | CCAACGTTTCGATGCGGTG |
| seuC R (SEQ ID NO: 58) | GCTGCTTAGGCTCACCGG |
| ssuD2 F (SEQ ID NO: 59) | CTATGAGCAAGTCGCGCAAG |
| ssuD2 R (SEQ ID NO: 60) | CTGGAAATAAACGGAGTCGCTAC |

[Deposit of Microorganisms]

Depository Institution: Korea Research Institute of Bioscience and Biotechnology Accession Number: KCTC 12970BP Deposit Date: Dec. 23, 2015.

INDUSTRIAL APPLICABILITY

According to the present invention, L-cysteine can be produced with high efficiency as a result of regulating metabolic fluxes associated with the L-cysteine metabolic pathway and regulating a system for supplying a sulfur source essential for synthesis of L-cysteine of the mutant microorganism.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A recombinant *Corynebacterium glutamicum* expressing cysE comprising the nucleotide sequence of SEQ ID NO:1 and encoding a serine acetyltransferase, cysK comprising the nucleotide sequence of SEQ ID NO:2 and encoding an acetylserine sulfhydrylase, and cysR comprising the nucleotide sequence of SEQ ID NO:3 and encoding a sulfur supply gene group-activating transcriptional regulator, wherein the *Corynebacterium glutamicum* produces L-cysteine from glucose.

2. A method for producing L-cysteine, comprising the steps of:
   (a) producing L-cysteine by culturing the recombinant *Corynebacterium glutamicum* of claim 1; and
   (b) recovering the produced L-cysteine.

* * * * *